United States Patent
Hills et al.

(10) Patent No.: US 7,557,066 B2
(45) Date of Patent: Jul. 7, 2009

(54) USE OF SULFONYLUREAS

(75) Inventors: Martin Hills, Idstein (DE); Hansjörg Krähmer, Hofheim (DE); Christian Waldraff, Bad Vilbel (DE); Hansjörg Dietrich, Hofheim (DE); Dieter Feucht, Kelkheim (DE); Klaus-Helmut Müller, Düsseldorf (DE); Ulrich Philipp, Lees Summit, MO (US)

(73) Assignee: Bayer CropScience AG (DE)

( * ) Notice: Subject to any disclaimer, the term of this patent is extended or adjusted under 35 U.S.C. 154(b) by 451 days.

(21) Appl. No.: 11/090,424

(22) Filed: Mar. 25, 2005

(65) Prior Publication Data

US 2005/0233908 A1    Oct. 20, 2005

(30) Foreign Application Priority Data

Mar. 27, 2004 (DE) .................. 10 2004 015 140
Jun. 30, 2004 (DE) .................. 10 2004 031 346

(51) Int. Cl.
*C07D 413/10* (2006.01)
*C07D 413/14* (2006.01)
*A01N 43/54* (2006.01)
*A01N 43/88* (2006.01)
*C07D 413/02* (2006.01)
*C07D 413/06* (2006.01)
*A01N 43/72* (2006.01)

(52) U.S. Cl. ........................ 504/223; 544/65
(58) Field of Classification Search ............... 504/230
See application file for complete search history.

(56) References Cited

U.S. PATENT DOCUMENTS

| 4,704,158 A | 11/1987 | Diehr et al. |
| 4,906,282 A | 3/1990 | Rorer |
| 5,476,936 A * | 12/1995 | Philipp et al. ............... 504/223 |
| 5,847,126 A | 12/1998 | Philipp et al. |

FOREIGN PATENT DOCUMENTS

| DE | 35 16435 | 3/1986 |
| EP | 0 173 958 | 3/1986 |
| EP | 0 301 784 | 2/1989 |
| EP | 0 612 473 A1 * | 2/1994 |
| EP | 0 645 386 A1 | 3/1995 |

OTHER PUBLICATIONS

U.S. Appl. No. 11/090,985, filed Mar. 25, 2005.
U.S. Appl. No. 11/090,374, filed Mar. 25, 2005.

* cited by examiner

*Primary Examiner*—Johann R Richter
*Assistant Examiner*—Courtney Brown
(74) *Attorney, Agent, or Firm*—Connolly Bove Lodge & Hutz LLP

(57) ABSTRACT

The invention relates to the use of compounds of the formula (I) and salts thereof, as defined in the application, for the selective control of unwanted vegetation in leguminous plants or for the non-selective control of unwanted vegetation

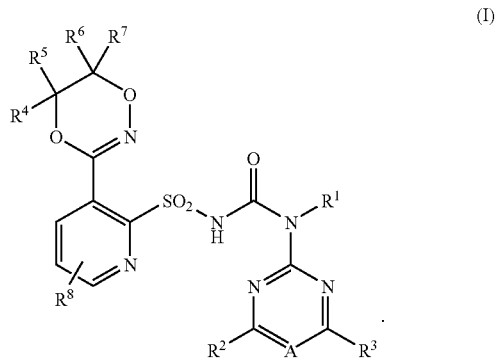

20 Claims, No Drawings

USE OF SULFONYLUREAS

The invention relates to the use of specific sulfonylureas for the non-selective control of unwanted vegetation and for the selective control of unwanted vegetation in leguminous plants.

It is known that certain N-azinyl-N'-arylsulfonylureas having simple open-chain hydroxamic ester groups in the aryl moiety, such as, for example, N-(4,6-dimethylpyrimidin-2-yl)-N'-(2-methoxyaminocarbonylphenylsulfonyl)-urea and the corresponding-N'-(2-N-octyloxyaminocarbonylphenyl-sulfonyl)-urea, have herbicidal properties (cf. DE-A-3 516 435, EP-A-173 958, U.S. Pat. No. 4,704,158). However, the herbicidal action of these known compounds is not entirely satisfactory.

Also known are furthermore herbicidally active N-azinyl-N'-(het)arylsulfonyl-ureas which are substituted in the (het) aryl moiety by O,O-dialkylated, likewise open-chain hydroxamic acid groups (cf. EP-A-301 784) or by cyclic dioxazine (cf. U.S. Pat. No. 5,476,936).

It was an object of the present invention to provide better control of unwanted vegetation including, for example, in crop plants. Surprisingly, it has been found that specific compounds of the formula (I) and salts thereof are suitable for use as agrochemically active compounds for the improved, in particular selective, control of unwanted vegetation in leguminous plants and also for the non-selective control of unwanted vegetation.

Accordingly, the present invention relates to the use of compounds of the formula (I) and salts thereof for the non-selective control of unwanted vegetation or for the selective control of unwanted vegetation in leguminous plants in which
A is nitrogen or a $CR^{11}$ grouping,
 where
  $R^{11}$ is hydrogen, alkyl, halogen or haloalkyl,
$R^1$ is hydrogen or an optionally substituted radical the group consisting of alkyl, alkoxy, alkoxyalkyl, alkenyl, alkynyl, cycloalkyl, cycloalkylalkyl, aralkyl and aryl,
$R^2$ is hydrogen, halogen or is in each case optionally halogen-substituted alkyl, alkoxy, alkylthio, alkylamino or dialkylamino having in each case 1 to 6 carbon atoms,
$R^3$ is hydrogen, halogen or is in each case optionally halogen-substituted alkyl, alkoxy, alkylthio, alkylamino or dialkylamino having in each case 1 to 6 carbon atoms,
$R^4$-$R^7$ independently of one another are hydrogen, halogen, cyano, thiocyanato or are in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
$R^8$ is hydrogen, halogen, cyano, thiocyanato or is in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms, where in the radicals mentioned above the alkyl and alkylene groups may each contain 1 to 6 carbon atoms, the alkenyl and alkynyl groups may each contain 2 to 6 carbon atoms, the cycloalkyl groups may each contain 3 to 6 carbon atoms and the aryl groups may each contain 6 or 10 carbon atoms.

The compounds of the formula (I) and their salts are known, as is their preparation, for example from U.S. Pat. No. 5,476,936, which is incorporated into the present description by way of reference.

The invention preferably provides the use of compounds of the formula (I) and salts thereof in which
A is nitrogen or a CH grouping,
$R^1$ is hydrogen or an optionally halogen-substituted radical from the group consisting of alkyl, alkoxy, alkoxyalkyl, alkenyl and alkynyl having in each case up to 3 carbon atoms,
$R^2$ is hydrogen, halogen or in each case optionally halogen-substituted alkyl, alkoxy, alkylthio, alkylamino or dialkylamino having in each case 1 to 3 carbon atoms in the alkyl radicals,
$R^3$ is hydrogen, halogen or in each case optionally halogen-substituted alkyl, alkoxy, alkylthio, alkylamino or dialkylamino having in each case 1 to 3 carbon atoms in the alkyl radicals,
$R^4$-$R^7$ independently of one another are hydrogen, halogen, cyano, thiocyanato or are in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals,
$R^8$ is hydrogen, halogen, cyano, thiocyanato or is in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals.

The invention furthermore preferably relates to the use of salts which are obtained by customary processes from compounds of the formula (I) and bases, such as, for example, sodium hydroxide, sodium hydride, sodium amide and sodium carbonate, potassium hydroxide, potassium hydride, potassium amide and potassium carbonate or calcium hydroxide, calcium hydride, calcium amide and calcium carbonate, sodium $C_1$-$C_4$-alkoxides or potassium $C_1$-$C_4$-alkoxides, ammonia, $C_1$-$C_4$-alkylamines, di-($C_1$-$C_4$-alkyl)amines or tri-($C_1$-$C_4$-alkyl)amines.

The invention relates in particular to the use of compounds of the formula (I) and salts thereof, in which
A is nitrogen or a CH grouping,
$R^1$ is hydrogen, methyl, ethyl, methoxy, methoxymethyl or ethoxy,
$R^2$ is hydrogen, chlorine, methyl, ethyl, trifluoromethyl, methoxy, ethoxy, difluoromethoxy, methylthio, methylamino or dimethylamino,
$R^3$ is hydrogen, chlorine, methyl, ethyl, trifluoromethyl, methoxy, ethoxy, difluoromethoxy, methylthio, methylamino or dimethylamino, $R^4$-$R^7$ independently of one another are hydrogen, fluorine, chlorine, cyano, or are in each case optionally chlorine- or fluorine-substituted methyl, methylthio, methylsulfinyl, methylsulfonyl, methoxycarbonyl or ethoxycarbonyl, preferably hydrogen, $R^8$ is hydrogen, fluorine, chlorine, bromine, cyano or is in each case optionally chlorine- or fluorine-substituted methyl, methoxy, ethoxy, methylthio, ethylthio, methylsulfinyl, ethylsulfinyl, methylsulfonyl, ethylsulfonyl, methyl- or dimethylamino, preferably hydrogen.

The invention relates particularly preferably to the use of compounds of the formula (I) and salts thereof, in particular alkali metal salts thereof, in which A is nitrogen, $R^1$ is hydrogen or methyl, $R^2$ is hydrogen, chlorine, methyl, ethyl, trifluoromethyl, methoxy, ethoxy, difluoromethoxy, methylthio, methylamino or dimethylamino, $R^3$ is hydrogen, chlorine, methyl, ethyl, trifluoromethyl, methoxy, ethoxy, difluoromethoxy, methylthio, methylamino or dimethylamino, $R^4$-$R^7$ are hydrogen, $R^8$ hydrogen.

Likewise, the invention particularly preferably relates to the use of compounds of the formula (I) and salts thereof, in particular alkali metal salts thereof, in which A is a CH grouping, $R^1$ is hydrogen or methyl, $R^2$ is hydrogen, chlorine, methyl, ethyl, trifluoromethyl, methoxy, ethoxy, difluoromethoxy, methylthio, methylamino or dimethylamino, $R^3$ is hydrogen, chlorine, methyl, ethyl, trifluoromethyl, methoxy, ethoxy, difluoromethoxy, methylthio, methylamino or dimethylamino, $R^4$-$R^8$ are hydrogen, $R^8$ is hydrogen.

The general or preferred radical definitions given above can be combined with one another as desired, i.e. including combinations between the given preferred ranges.

The hydrocarbon radicals mentioned in the definitions of the radicals, such as alkyl, alkenyl or alkynyl, are in each case straight-chain or branched even if this is not expressly mentioned, including in combination with heteroatoms, such as in alkoxy, alkylthio, haloalkyl or alkylamino.

If appropriate, the compounds of the formula (I) can be converted into salts, for example metal salts, such as alkali metal (for example, Na, K) salts or alkaline earth metal (for example Ca, Mg) salts or ammonium or amine salts. Such salts are obtained in a simple manner by customary methods for forming salts, for example by dissolving or dispersing a compound of the formula (I) in a suitable diluent, such as, for example, methylene chloride, acetone, tert-butyl methyl ether or toluene, and adding a suitable base. The salts can then—if appropriate after prolonged stirring—be isolated by concentration or filtration with suction.

Active compounds preferably used according to the invention are listed in the table below, where the following abbreviations are used:

TABLE 1

Examples of the compounds of the formula (I) where $R^4 = R^5 = R^6 = R^7 = R^8 = H$

| Ex. No. | $R^1$ | A | $R^2$ | $R^3$ | m.p. (° C.) |
|---|---|---|---|---|---|
| I-1 | H | CH | $OCH_3$ | $OC_2H_5$ | 154 |
| I-2 | H | CH | $OCH_3$ | $CH_3$ | |
| I-3 | H | CH | $OHC_3$ | $CH_3$ | 180-181$^{(+)}$ |
| I-4 | H | CH | $OCH_3$ | $C_2H_5$ | |
| I-5 | H | CH | $OCH_3$ | $CF_3$ | |
| I-6 | H | CH | $OCH_3$ | $OCF_2H$ | |
| I-7 | H | CH | $OCH_3$ | $NHCH_3$ | |
| I-8 | H | CH | $OCH_3$ | $N(CH_3)_2$ | 199.5 |
| I-9 | H | CH | $OCH_3$ | Cl | 110-111 |
| I-10 | H | CH | $OCH_3$ | Cl | 175-178$^{(+)}$ |
| I-11 | H | CH | $OCH_3$ | $OCH_3$ | 167-168 |
| I-12 | H | CH | $OCH_3$ | $OCH_3$ | 171-172$^{(+)}$ |
| I-13 | H | CH | $OC_2H_5$ | $OC_2H_5$ | |
| I-14 | H | CH | $OC_2H_5$ | $OC_2H_5$ | 152-154$^{(+)}$ |
| I-15 | H | CH | $OC_2H_5$ | $CH_3$ | |
| I-16 | H | CH | $OC_2H_5$ | $C_2H_5$ | |
| I-17 | H | CH | $OC_2H_5$ | $CF_3$ | |
| I-18 | H | CH | $OC_2H_5$ | $OCF_2H$ | |
| I-19 | H | CH | $OC_2H_5$ | $NHCH_3$ | |
| I-20 | H | CH | $OC_2H_5$ | $N(CH_3)_2$ | |
| I-21 | H | CH | $OC_2H_5$ | Cl | 158-159 |
| I-22 | H | CH | $OC_2H_5$ | Cl | 213$^{(+)}$ |
| I-23 | H | CH | $CH_3$ | $CH_3$ | 153 |
| I-24 | H | CH | $CH_3$ | $C_2H_5$ | |
| I-25 | H | CH | $CH_3$ | $CF_3$ | |
| I-26 | H | CH | $CH_3$ | $OCF_2H$ | |
| I-27 | H | CH | $CH_3$ | $NHCH_3$ | |
| I-28 | H | CH | $CH_3$ | $N(CH_3)_2$ | |
| I-29 | H | CH | $CH_3$ | Cl | 108-109 |
| I-30 | H | CH | $CH_3$ | Cl | >300$^{(+)}$ |
| I-31 | H | CH | $C_2H_5$ | $C_2H_5$ | |
| I-32 | H | CH | $C_2H_5$ | $CF_3$ | |
| I-33 | H | CH | $C_2H_5$ | $OCF_2H$ | |
| I-34 | H | CH | $C_2H_5$ | $NHCH_3$ | |
| I-35 | H | CH | $C_2H_5$ | Cl | |
| I-36 | H | CH | $CF_3$ | $CF_3$ | |
| I-37 | H | CH | $CF_3$ | $OCF_2H$ | |
| I-38 | H | CH | $CF_3$ | $NHCH_3$ | |
| I-39 | H | CH | $CF_3$ | $N(CH_3)_2$ | |
| I-40 | H | CH | $CF_3$ | Cl | |
| I-41 | H | CH | $OCF_2H$ | $OCF_2H$ | |
| I-42 | H | CH | $OCF_2H$ | $NHCH_3$ | |
| I-43 | H | CH | $OCF_2H$ | $N(CH_3)_2$ | |
| I-44 | H | CH | $OCF_2H$ | Cl | |
| I-45 | H | CH | $NHCH_3$ | $NHCH_3$ | |
| I-46 | H | CH | $NHCH_3$ | $N(CH_3)_2$ | |
| I-47 | H | CH | $NHCH_3$ | Cl | |
| I-48 | H | CH | $N(CH_3)_2$ | $N(CH_3)_2$ | |
| I-49 | H | CH | $N(CH_3)_2$ | Cl | |
| I-50 | H | CH | Cl | Cl | |
| I-51 | H | N | $OCH_3$ | $OCH_3$ | 255 |
| I-52 | H | N | $OCH_3$ | $OCH_3$ | 159-162$^{(+)}$ |
| I-53 | H | N | $OCH_3$ | $OC_2H_5$ | |
| I-54 | H | N | $OCH_3$ | $CH_3$ | |
| I-55 | H | N | $OCH_3$ | $C_2H_5$ | |
| I-56 | H | N | $OCH_3$ | $CF_3$ | |
| I-57 | H | N | $OCH_3$ | $OCF_2H$ | |
| I-58 | H | N | $OCH_3$ | $NHCH_3$ | |
| I-59 | H | N | $OCH_3$ | $N(CH_3)_2$ | |
| I-60 | H | N | $OCH_3$ | $N(CH_3)_2$ | 156$^{(+)}$ |
| I-61 | H | N | $OCH_3$ | Cl | |
| I-62 | H | N | $OC_2H_5$ | $OC_2H_5$ | |
| I-63 | H | N | $OC_2H_5$ | $CH_3$ | |
| I-64 | H | N | $OC_2H_5$ | $C_2H_5$ | |
| I-65 | H | N | $OC_2H_5$ | $CF_3$ | |
| I-66 | H | N | $OC_2H_5$ | $OCF_2H$ | |
| I-67 | H | N | $OC_2H_5$ | $NHCH_3$ | |
| I-68 | H | N | $OC_2H_5$ | $N(CH_3)_2$ | |
| I-69 | H | N | $OC_2H_5$ | Cl | |
| I-70 | H | N | $OC_2H_5$ | Cl | 213$^{(+)}$ |
| I-71 | H | N | $CH_3$ | $CH_3$ | |
| I-72 | H | N | $CH_3$ | $C_2H_5$ | |
| I-73 | H | N | $CH_3$ | $CF_3$ | |
| I-74 | H | N | $CH_3$ | $OCF_2H$ | |

TABLE 1-continued

Examples of the compounds of the formula (I) where
$R^4 = R^5 = R^6 = R^7 = R^8 = H$

| Ex. No. | $R^1$ | A | $R^2$ | $R^3$ | m.p. (° C.) |
|---|---|---|---|---|---|
| I-75 | H | N | $CH_3$ | $NHCH_3$ | |
| I-76 | H | N | $CH_3$ | $N(CH_3)_2$ | |
| I-77 | H | N | $CH_3$ | Cl | |
| I-78 | H | N | $C_2H_5$ | $C_2H_5$ | |
| I-79 | H | N | $C_2H_5$ | $CF_3$ | |
| I-80 | H | N | $C_2H_5$ | $OCF_2H$ | |
| I-81 | H | N | $C_2H_5$ | $NHCH_3$ | |
| I-82 | H | N | $C_2H_5$ | Cl | |
| I-83 | H | N | $CF_3$ | $CF_3$ | |
| I-84 | H | N | $CF_3$ | $OCF_2H$ | |
| I-85 | H | N | $CF_3$ | $NHCH_3$ | |
| I-86 | H | N | $CF_3$ | $N(CH_3)_2$ | |
| I-87 | H | N | $CF_3$ | Cl | |
| I-88 | H | N | $OCF_2H$ | $OCF_2H$ | |
| I-89 | H | N | $OCF_2H$ | $NHCH_3$ | |
| I-90 | H | N | $OCF_2H$ | $N(CH_3)_2$ | |
| I-91 | H | N | $OCF_2H$ | Cl | |
| I-92 | H | N | $NHCH_3$ | $NHCH_3$ | |
| I-93 | H | N | $NHCH_3$ | $N(CH_3)_2$ | |
| I-94 | H | N | $NHCH_3$ | Cl | |
| I-95 | H | N | $N(CH_3)_2$ | $N(CH_3)_2$ | |
| I-96 | H | N | $N(CH_3)_2$ | Cl | |
| I-97 | H | N | Cl | Cl | |
| I-98 | $CH_3$ | N | $OCH_3$ | $OCH_3$ | |
| I-99 | $CH_3$ | N | $OCH_3$ | $OC_2H_5$ | |
| I-100 | $CH_3$ | N | $OCH_3$ | $CH_3$ | |
| I-101 | $CH_3$ | N | $OCH_3$ | $C_2H_5$ | |
| I-102 | $CH_3$ | N | $OCH_3$ | $CF_3$ | |
| I-103 | $CH_3$ | N | $OCH_3$ | $OCF_2H$ | |
| I-104 | $CH_3$ | N | $OCH_3$ | $NHCH_3$ | |
| I-105 | $CH_3$ | N | $OCH_3$ | $N(CH_3)_2$ | |
| I-106 | $CH_3$ | N | $OCH_3$ | Cl | |
| I-107 | $CH_3$ | N | $OC_2H_5$ | $OC_2H_5$ | |
| I-108 | $CH_3$ | N | $OC_2H_5$ | $CH_3$ | |
| I-109 | $CH_3$ | N | $OC_2H_5$ | $C_2H_5$ | |
| I-110 | $CH_3$ | N | $OC_2H_5$ | $CF_3$ | |
| I-111 | $CH_3$ | N | $OC_2H_5$ | $OCF_2H$ | |
| I-112 | $CH_3$ | N | $OC_2H_5$ | $NHCH_3$ | |
| I-113 | $CH_3$ | N | $OC_2H_5$ | $N(CH_3)_2$ | |
| I-114 | $CH_3$ | N | $OC_2H_5$ | Cl | |
| I-115 | $CH_3$ | N | $CH_3$ | $CH_3$ | |
| I-116 | $CH_3$ | N | $CH_3$ | $C_2H_5$ | |
| I-117 | $CH_3$ | N | $CH_3$ | $CF_3$ | |
| I-118 | $CH_3$ | N | $CH_3$ | $OCF_2H$ | |
| I-119 | $CH_3$ | N | $CH_3$ | $NHCH_3$ | |
| I-120 | $CH_3$ | N | $CH_3$ | $N(CH_3)_2$ | |
| I-121 | $CH_3$ | N | $CH_3$ | Cl | |
| I-122 | $CH_3$ | N | $C_2H_5$ | $C_2H_5$ | |
| I-123 | $CH_3$ | N | $C_2H_5$ | $CF_3$ | |
| I-124 | $CH_3$ | N | $C_2H_5$ | $OCF_2H$ | |
| I-125 | $CH_3$ | N | $C_2H_5$ | $NHCH_3$ | |
| I-126 | $CH_3$ | N | $C_2H_5$ | Cl | |
| I-127 | $CH_3$ | N | $CF_3$ | $CF_3$ | |
| I-128 | $CH_3$ | N | $CF_3$ | $OCF_2H$ | |
| I-129 | $CH_3$ | N | $CF_3$ | $NHCH_3$ | |
| I-130 | $CH_3$ | N | $CF_3$ | $N(CH_3)_2$ | |
| I-131 | $CH_3$ | N | $CF_3$ | Cl | |
| I-132 | $CH_3$ | N | $OCF_2H$ | $OCF_2H$ | |
| I-133 | $CH_3$ | N | $OCF_2H$ | $NHCH_3$ | |
| I-134 | $CH_3$ | N | $OCF_2H$ | $N(CH_3)_2$ | |
| I-135 | $CH_3$ | N | $OCF_2H$ | Cl | |
| I-136 | $CH_3$ | N | $NHCH_3$ | $NHCH_3$ | |
| I-137 | $CH_3$ | N | $NHCH_3$ | $N(CH_3)_2$ | |
| I-138 | $CH_3$ | N | $NHCH_3$ | Cl | |
| I-139 | $CH_3$ | N | $N(CH_3)_2$ | $N(CH_3)_2$ | |
| I-140 | $CH_3$ | N | $N(CH_3)_2$ | Cl | |
| I-141 | $CH_3$ | N | Cl | Cl | |
| I-142 | H | N | $N(CH_3)_2$ | $OCH_2CF_3$ | 158 |
| I-143 | H | CH | Cl | $OCH_2CF_3$ | 204-205 |
| I-144 | H | CH | Cl | $OCH_2CF_3$ | |
| I-145 | H | CH | Cl | $OCH_2CF_3$ | 207[(+)] | m.p.: = melting point

[(+)]= the stated melting point (m.p.) refers in each case to the corresponding sodium salt, i.e. the corresponding compound in which the hydrogen of the —$SO_2NH$ group is replaced by sodium.

The compounds of the formula (I) and their salts can be used for controlling unwanted vegetation. Unwanted plants are to be understood as meaning all plants growing in locations where they are unwanted. These may be, for example, harmful plants (for example weeds or unwanted crop plants) including, for example, those which are resistant to certain herbicidally active compounds, such as glyphosate, atrazine, glufosinate or imidazolinone herbicides. The compounds of the formula (I) can be used, for example, against the following plants:

Monocotyledonous weeds, for example of the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

Dicotyledonous weeds, for example of the genera *Sinapsis, Lepidium, Galium, Stellaria, Matricaria, Anthemis, Galinsoga, Chenopodium, Urtica, Senecio, Amaranthus Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia.*

Monocotyledonous crop plants, for example monocotyledonous transgenic and nontransgenic crop plants, for example of the genera *Oryza, Zea, Triticum, Hordeum, Avena, Secale, Sorghum, Panicum, Saccharum, Ananas, Asparagus, Allium.*

Dicotyledonous crop plants, for example of the genera *Gossypium, Beta, Solanum, Nicotiana, Lycopersicon, Brassica, Lactuca, Cucumis, Cucurbita.*

However, the use of the compounds of the formula (I) and their salts is by no means limited to these genera but extends likewise to other plants different from leguminous plants.

The compounds of the formula (I) and their salts have excellent selectivity in crops of leguminous plants. They are suitable, for example, for the selective control of unwanted vegetation, for example of harmful plants (for example monocotyledonous and dicotyledonous weeds or unwanted crop plants) in crops of transgenic and nontransgenic leguminous plants, in particular of the genus *Glycine*, for example by the pre-sowing method, the pre-emergence method or the post-emergence method.

Suitable leguminous plants are, for example, transgenic and nontransgenic leguminous plants, for example of the genera *Glycine, Phaseolus, Pisum, Vicia* and *Arachis*. Preferred are leguminous plants of the genus *Glycine*, for example of the species *Glycine max.* (soybean), such as nontransgenic *Glycine max.* (for example conventional cultivars, such as STS cultivars) or transgenic *Glycine max.* (for example RR-soybeans or LL-soybeans) and crossbreeds thereof.

The compounds of the formula (I) and their salts can also be employed non-selectively for controlling unwanted vegetation, for example in permanent crops and plantation crops, on roadside, squares, industrial sites, airports or railway tracks, or for the burn-down application, for example in farm crops, for example monocotyledonous farm crops, such as cereals (for example wheat, barley, rye, oats), rice, corn, millet, or dicotyledonous farm crops, such as sugarbeet, oilseed rape, cotton, sunflowers and leguminous plants, for example of the genera *Glycine* (for example *Glycine max.* (soybean), such as nontransgenic *Glycine max.* (for example conventional cultivars, such as STS cultivars) or transgenic *Glycine max.* (for example RR-soybean or LL-soybean) and crossbreeds thereof, *Phaseolus, Pisum, Vicia* and *Arachis*, or vegetable crops from various botanical groups, such as potato, leek, cabbage, carrot, tomato, onion. Here, the application is preferably to the emerged harmful plants (for example weeds or unwanted crop plants), in particular prior to the emergence of the (wanted) crop plants.

Permanent crops and plantation crops are, for example, pomaceous fruit and stone fruit, berry fruit, grapevines, Hevea, bananas, sugar cane, coffee, tea, citrus fruit, nut plantations, roses, palm plantations and forest plantations.

A preferred use in the non-selective area is the burn-down application in crop plants where the compounds of the formula (I) and their salts are applied to the emerged harmful plants prior to the emergence of the crop plants; preference is given here to application prior to sowing of the crop plants or during sowing of the crop plants.

The compounds of the formula (I) and their salts can be converted into customary formulations, such as solutions, emulsions, suspensions, powders, foams, pastes, granules, aerosols, natural and synthetic materials impregnated with active compound and microencapsulations in polymeric materials. The formulations may comprise the customary auxiliaries and additives.

These formulations are produced in a known manner, for example by mixing the active compounds with extenders, that is liquid, solvents, pressurized liquefied gases and/or solid carriers, optionally with the use of surfactants, that is emulsifiers and/or dispersants and/or foam formers.

If the extender used is water, it is also possible to employ, for example, organic solvents as auxiliary solvents. Suitable liquid solvents are essentially: aromatics, such as xylene, toluene, alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide or dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated rocks, such as calcite, marble, pumice, sepiolite and dolomite, and also synthetic granules of inorganic and organic meals, and granules of organic materials, such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, and also protein hydrolysates; suitable dispersants are: for example lignosulfite waste liquors and methylcellulose.

Tackifiers such as carboxymethylcellulose and natural and synthetic polymers in the form of powders, granules or lattices, such as gum arabic, polyvinyl alcohol and polyvinyl acetate or else natural phospholipids, such as cephalins and lecithins and synthetic phospholipids can be used in the formulations. Other possible additives are mineral and vegetable oils.

It is possible to use colorants, such as inorganic pigments, for example iron oxide, titanium oxide and Prussian Blue, and organic dyes, such as alizarin dyes, azo dyes and metal phthalocyanine dyes, and trace nutrients, such as salts of iron, manganese, boron, copper, cobalt, molybdenum and zinc.

The formulations generally comprise between 0.1 and 95 percent by weight of active compound, preferably between 0.5 and 90%.

The active compounds of the formula (I) and their salts, as such or in their formulations, may also be used as a mixture with other agrochemically active compounds, such as known herbicides, for controlling unwanted vegetation, for example for controlling weeds or for controlling unwanted crop plants, ready mixes or tank mixes, for example, being possible. Suitable for use as combination partners for the active compounds of the formula (I) and their salts, for example in mixed formulations or a tank mix, are, for example, known agrochemically active compounds, as described, for example, in Weed Research 26, 441-445 (1986) or "The Pesticide Manual", 13th edition, The British Crop Protection Council, 2003, and the literature cited therein. The following active compounds, for example, may be mentioned as herbicides known from the literature which may be combined with the active compounds of the formula (I) and salts thereof (note: the compounds are referred to either by the "common name" of the International Organization for Standardization (ISO) or by the chemical name, if appropriate together with a customary code number, and include in each case all possible use forms, such as acids, salts, esters and isomers, such as stereoisomers and optical isomers. One and, in some cases, more application forms are mentioned):

2,4-D, acetochlor, acifluorfen, acifluorfen-sodium, aclonifen, alachlor, alloxydim, alloxydim-sodium, ametryn, amicarbazone, amidosulfuron, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenioxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlorotoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, triaziflam;, diquat-dibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, flamprop-M-isopropyl, flamprop-M-methyl, flazasulfuron, florasulam, fluazifop, fluazifop-butyl, fluazifop-butyl, fluazolate, fluoarbazone-sodium, flucetosulfuron, fluchloralin, flufenacet, flufenpyr, flumetsulam, flumiclorac-pentyl, flumioxazin, fluometuron, fluorochloridone, fluoroglycofen-ethyl, flupoxam, flupyrsulfuron-methyl-sodium, fluridone, fluroxypyr, fluroxypyr-butoxypropyl, fluroxypyr-meptyl, flurprimidol, flurtamone, fluthiacet-methyl, fomesafen, foramsulfuron, glufosinate, glufosinate-ammonium, glyphosate, halosulfuron-methyl, halyoxfop, halyoxfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, iodosulfuron-methyl-sodium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenychlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl and tritosulfuron.

Preferred combination partners are compounds which are selective in soybeans, for example (Ba) herbicides which are selective in soybeans against monocotyledonous and dicotyledonous harmful plants, for example trifluralin, metribuzin, clomazone, pendimethalin, metolachlor flumetsulam, dimethenamid, linuron, ethalfluralin, flufenacet, norflurazon, vernolate, chlortoluron, chlorotoluron, cloransulam and esters, such as the methyl ester, imazethapyr, imazamox, imazaquin, (Bb) herbicides which are selective in soybeans against dicotyledonous harmful plants, for example sulfentrazone, bentazone, thifensulfuron and its esters, in particular the methyl ester, oxyfluorfen, lactofen, fomesafen, flumiclorac and its esters, such as the pentyl ester, acifluorfen and its sodium salt, 2,4-DB and its esters and salts, flumioxazin, benazolin, 2,4-D and its esters and salts, chlorimuron and its esters and salts, such as chlorimuron-ethyl, (Bc) herbicides which are selective in soybeans against monocotyledonous harmful plants, for example sethoxydim, cycloxydim, clethodim, quizalofop-P and its esters, such as the ethyl or tefuryl ester, fenoxaprop-P and its esters, such as the ethyl ester, fluazifop-P and its esters, such as the butyl ester, haloxyfop and haloxyfop-P and their esters, such as the methyl or the etotyl ester, propaquizafop, alachlor, (Bd) non-selective herbicides which can also be used, for example, for specific purposes in soybeans, for example glufosinate, glyphosate, paraquat (salts), such as paraquat dichloride.

Other preferred combination partners are benozalin, fenoxaprop, lactofen, chlortoluron, flufenacet, metribuzin, benfuresate, fentrazamid, mefenacet, diclofop, ioxynil, bromoxynil, amidosulfuron, flurtamone, diflufenican, ethoxysulfuron, flucarbazone, propoxycarbazone, sulcotrione, mesotrione, isoproturon, iodosulfuron, mesosulfuron, foramsulfuron, amidofos, anilofos, oxaziclomefone, oxadiargyl, isoxaflutole, linuron.

Mixtures with other known active compounds, such as fungicides, insecticides, acaricides, nematicides, safeners, bird repellents, plant nutrients and agents which improve the soil structure are also possible.

The active compounds of the formula (I) and their salts can be applied as such, in the form of their formulations or in the use forms prepared therefrom by further dilution, such as ready-to-use solutions, suspensions, emulsions, powders, pastes and granules. Application is carried out in the customary manner, for example by watering, spraying, atomizing, broadcasting.

The present invention furthermore relates to a method for controlling unwanted egetation (for example for the non-selective control of harmful plants or for the selective control of harmful plants in leguminous plants) which comprises applying one or more compounds of the formula (I) or salts thereof to the plants (for example harmful plants, such as monocotyledonous or dicotyledonous weeds or unwanted crop plants), the seed (for example grains, seed or vegetative propagation organs, such as tubers or shoot parts with buds) or the area in which the plants grow (for example the area under cultivation). They can be applied, for example, before sowing and also both before and after emergence of the plants. Pre-sowing application can be carried out, for example, by spraying or incorporation into the soil. Split applications, for example early pre-emergence followed by later post-emergence application, are also possible. Preferred is an application to the emerged harmful plants, in particular prior to the emergence of (wanted) crop plants, such as leguminous plants.

Preferred for selective application in leguminous plants is an application to emerged plants, in particular to emerged harmful plants (for example weeds or unwanted crop plants), preferably prior to the emergence of the leguminous plants. For the non-selective application, preference is given to application to the emerged harmful plants (for example weeds or unwanted crop plants). In the burn-down application, the application is to the emerged harmful plants, preferably prior to sowing or during sowing of the crop plants.

The amount of active compound applied can be varied within a relatively wide range. It depends essentially on the nature of the desired effect. In general, the application rates are between 0.01 g and 100 g of active compound per hectare of soil area. For a selective application, preference is generally given to lower application rates, for example in the range from 0.01 to 9 g of active compound per hectare, preferably between 0.1 and 5 g per hectare, in particular in the application to emerged plants, in particular emerged harmful plants (for example weeds or unwanted crop plants). Preferred application rates for the non-selective application are generally in the range from 0.01 g to 3490 g of active compound per hectare, in particular from 0.01 g to 9 g of active compound per hectare, preferably between 0.1 g and 5 g per hectare.

The active compounds of the formula (I) and their salts have excellent selectivity in leguminous plants, an excellent activity against the harmful plants typically occurring in leguminous plants being surprisingly retained even at low dosages of active compound. In particular, harmful plants which occur in crops of leguminous plants and which are frequently difficult to control, such as species of the genera *Amaranthus, Echinochloa, Sorghum, Ipomoea, Pharbitis, Solanum, Setaria, Brachiaria, Lolium, Euphorbia, Abutilon* are controlled effectively.

Moreover, the compounds have excellent activity when applied non-selectively, for example in permanent crops and plantation crops or on roadsides, squares, industrial sites, airports or railway tracks, or in the burn-down application.

BIOLOGICAL EXAMPLES

1. Pre-Emergence Effect on Weeds

Seeds or rhizome pieces of monocotyledonous and dicotyledonous weed plants were placed in sandy loam soil in cardboard pots and covered with soil. The compounds of the formula (I) or their salts, formulated in the form of wettable powders or emulsion concentrates, were then applied to the surface of the soil cover in the form of aqueous suspensions or emulsions at an application rate of 600 to 800 l of water/ha (converted) in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the test results, the compounds tested have good herbicidal pre-emergence activity against a broad spectrum of weed grasses and broad-leaved weeds. For example, the compounds Nos. I-1, I-3, I-8, I-9, I-10, I-11, I-12, I-14, I-21, I-22, I-23, I-29, I-30, I-51, I-52, I-60, I-70, I-142, I-143, I-145 and other compounds from Table 1 have very good herbicidal action against harmful plants such as *Sinapsis alba, Chrysanthemum segetum, Avena sativa, Stellaria media, Echinochloa crus-galli, Lolium multiflorum, Setaria viridis, Abutilon theophrasti, Amaranthus retroflexus, Brachiaria plantaginea, Solanum nigrum, Euphorbia heterophylla, Sorghum halepense* and *Panicum miliaceum* in the pre-emergence method at an application rate of 100 g or less of active substance per hectare.

2. Post-Emergence Effect on Weeds

Seeds or rhizome pieces of monocotyledonous and dicotyledonous weeds were placed in a sandy loam soil in plastic pots, covered with soil and cultivated in a greenhouse under good growth conditions. Three weeks after sowing, the test plants were treated at the three-leaf stage. The compounds of the formula (I) or their salts, formulated as wettable powders or as emulsion concentrates, were sprayed, at various dosages, onto the green parts of the plants at an application rate of 600 to 800 l of water/ha (converted). After the test plants had remained in the greenhouse for about 3 to 4 weeks under optimum growth conditions, the effect of the preparations was scored visually by comparison with untreated controls. The tested compounds also have good herbicidal post-emergence activity against a broad spectrum of economically important weed grasses and broad-leaved weeds. The compounds Nos. I-1, I-3, I-8, I-9, I-10, I-11, I-12, I-14, I-21, I-22, I-23, I-29, I-30, I-51, I-52, I-60, I-70, I-142, I-143, I-145 and other compounds from Table 1, for example, have very good herbicidal action against harmful plants such as *Sinapsis alba, Echinochloa crus-galli, Lolium multiflorum, Chrysanthemum segetum, Setaria viridis, Abutilon theophrasti, Amaranthus retroflexus, Panicum miliaceum, Brachiaria plantaginea, Solanum nigrum, Euphorbia heterophylla, Sorghum halepense* and *Avena sativa* when applied by the post-emergence method at an application rate of 100 g or less of active substance per hectare. At an application rate of 30 g of active substance per hectare, for example, the compound I-9 exhibits a herbicidal activity of 100% against *Echinochloa crus-galli*, of 100% against *Brachiaria plantaginea*, of 100% against *Setaria viridis*, of 93% against *Amaranthus retroflexus* and of 100% against *Solarium nigrum*.

3. Crop Plant Compatibility

In further greenhouse experiments, seeds of a substantial number of crop plants and weeds were placed into sandy loam soil and covered with soil. Some of the pots were treated immediately as described under Section 1, and the remaining pots were placed in a greenhouse until the plants had developed two to three true leaves and then sprayed with various dosages of the compounds of the formula (I) or salts thereof, as described in Section 2. Visual scoring four to five weeks after the application and after the plants had been in the greenhouse revealed that the compounds tested, for example the compounds I-1, I-3, I-8, I-8, I-9, I-10, I-11, I-12, I-14, I-21, I-22, I-23, I-29, I-30, I-51, I-52, I-60, I-70, I-142, I-143, I-145 and other compounds from Table 1, applied by the pre-emergence or the post-emergence method, did not damage crops of leguminous plants, such as soybeans. At an application rate of 8 g of active substance per hectare, for example, compound I-9 exhibits 0% damage to soybeans (*Glycine max.*).

Examples Perennial plants were grown in pots under greenhouse conditions and treated with 10 g of a.i./ha (converted) of the substances according to the invention. Four weeks after the application, the above-ground parts of the plants were cut off. After a further four weeks, the inhibition of revegetation was scored in percent of the control, 100% corresponding to a total inhibition of revegetation.

| Substances | Application rate g of a.i./ha | LOLPE | CIRAR |
|---|---|---|---|
| Glyphosate | 600 | 35 | 25 |
| AE 1346151 | 10 | 100 | 70 |

The invention claimed is:

1. A method of using one or more compounds of the formula (I) or salts thereof for the non-selective control of unwanted vegetation or for the selective control of unwanted vegetation in leguminous plants

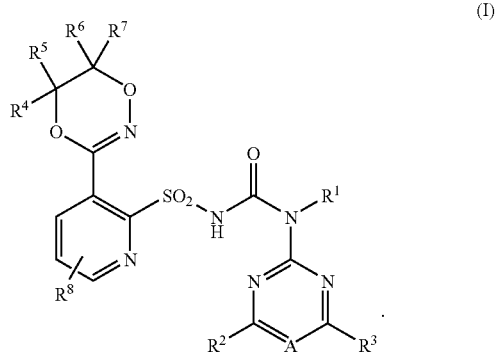

(I)

in which
- A is a $CR^{11}$ grouping, where
  $R^{11}$ is hydrogen,
- $R^1$ is hydrogen or an optionally substituted radical from the group consisting of alkyl, alkoxy, alkoxyalkyl, alkenyl, alkynyl, cycloalkyl, cycloalkylalkyl, aralkyl and aryl,
- $R^2$ is hydrogen, halogen or is in each case optionally halogen-substituted alkyl, alkoxy, alkylthio, alkylamino or dialkylamino having in each case 1 to 6 carbon atoms,
- $R^3$ is hydrogen, halogen or is in each case optionally halogen-substituted alkyl, alkoxy, alkylthio, alkylamino or dialkylamino having in each case 1 to 6 carbon atoms,
- $R^4$-$R^7$ independently of one another are hydrogen, halogen, cyano, thiocyanato or are in each case optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms, and
- $R^8$ is hydrogen, halogen, cyano, thiocyanato or in each optionally halogen-substituted alkyl, alkoxy, alkylthio, alkylsulfinyl, alkylsulfonyl, alkylamino, alkylcarbonyl, alkoxycarbonyl, alkylaminocarbonyl having in each case 1 to 3 carbon atoms,
- where in the radicals mentioned above the alkyl and alkylene groups may each contain 1 to 6 carbon atoms, the alkenyl and alkynyl groups may each contain 2 to 6 carbon atoms, the cycloalkyl groups may each contain 3 to 6 carbon atoms and the aryl groups may each contain 6 or 10 carbon atoms, said method comprising the step of applying said one or more compounds of formula (I) or salts thereof to the unwanted vegetation or to seeds of the unwanted vegetation or to an area in which the unwanted vegetation grows.

2. The method according to claim 1, where in formula (I)
- A is a CH grouping,
- $R^1$ is hydrogen or an optionally halogen-substituted radical from the group consisting of alkyl, alkoxy, alkoxyalkyl, alkenyl and alkynyl having in each case up to 3 carbon atoms,
- $R^2$ is hydrogen, halogen or in each case optionally halogen-substituted alkyl, alkoxy, alkylthio, alkylamino or dialkylamino having in each case 1 to 3 carbon atoms in the alkyl radicals,
- $R^3$ is hydrogen, halogen or in each case optionally halogen-substituted alkyl, alkoxy, alkylthio, alkylamino or dialkylamino having in each case 1 to 3 carbon atoms in the alkyl radicals,
- $R^4$-$R^7$ independently of one another are hydrogen, halogen, cyano, thiocyanato or are in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals, and
- $R^8$ is hydrogen, halogen, cyano, thiocyanato or is in each case optionally halogen-substituted alkyl, alkoxy, alkylthio, alkylsulfinyl, alkylsulfonyl, alkylamino, alkylcarbonyl, alkoxycarbonyl or alkylaminocarbonyl having in each case 1 to 3 carbon atoms in the alkyl radicals.

3. The method according to claim 1, where in formula (I)
- A is a CH grouping,
- $R^1$ is hydrogen, methyl, ethyl, methoxy, methoxymethyl or ethoxy,
- $R^2$ is hydrogen, chlorine, methyl, ethyl, trifluoromethyl, methoxy, ethoxy, difluoromethoxy, methylthio, methylamino or dimethylamino,
- $R^3$ is hydrogen, chlorine, methyl, ethyl, trifluoromethyl, methoxy, ethoxy, difluoromethoxy, methylthio, methylamino or dimethylamino,
- $R^4$-$R^7$ independently of one another are hydrogen, fluorine, chlorine, cyano, or are in each case optionally chlorine- or fluorine-substituted methyl, methylthio, methylsulfinyl, methylsulfonyl, methoxycarbonyl or ethoxycarbonyl, and
- $R^8$ is hydrogen, fluorine, chlorine, bromine, cyano or is in each case optionally chlorine- or fluorine-substituted methyl, methoxy, ethoxy, methylthio, ethylthio, methylsulfinyl, ethylsulfinyl, methylsulfonyl, ethylsulfonyl, methyl- or dimethylamino.

4. The method according to claim 1, where the leguminous plants are selected from the genera *Glycine, Phaseolus, Pisum, Vicia* and *Arachis*.

5. The method according to claim 1, wherein the unwanted vegetation is weeds or unwanted crop plants.

6. The method according to claim 1, where the one or more compounds of the formula (I) or salts thereof are applied to the unwanted vegetation.

7. A method for the non-selective control of unwanted vegetation or for the selective control of unwanted vegetation in leguminous plants or for the non-selective control of unwanted vegetation, which method comprises applying one or more compounds of the formula (I) or salts thereof as defined in claim 1 to seeds of the unwanted vegetation.

8. The method according to claim 7, where the leguminous plants are selected from the genera *Glycine, Phaseolus, Pisum, Vicia* and *Arachis*.

9. The method according to claim 7, where the unwanted vegetation is weeds or unwanted crop plants.

10. The method according to claim 7, where the one or more compounds of the formula (I) or salts thereof are applied to the seeds of the unwanted vegetation prior to emergence of the leguminous plants from soil.

11. The method according to claim 1, wherein the one or more compounds of formula (I) or salts thereof are applied to seeds of the unwanted vegetation.

12. The method according to claim 1, wherein the one or more compounds of formula (I) or salts thereof are applied to an area in which the unwanted vegetation grows.

13. The method according to claim 1, wherein the one or more compounds of formula (I) or salts thereof are applied to the unwanted vegetation or seeds of the unwanted vegetation at the same time that seeds for the leguminous plants are sowed.

14. The method according to claim 1, wherein the one or more compounds of formula (I) or salts thereof are applied to the unwanted vegetation or seeds of the unwanted vegetation after seeds for the leguminous plants are sowed.

15. The method according to claim 1, wherein the one or more compounds of formula (I) or salts thereof are applied to the unwanted vegetation or seeds of the unwanted vegetation after the leguminous plants have emerged from soil.

16. The method of claim 1, wherein the area in which the unwanted vegetation grows is an area in which the leguminous plants are growing or in which seeds of the leguminous plants have been or will be sowed.

17. The method of claim 1, wherein the one or more compounds of formula (I) or salts thereof are applied as a formulation to the unwanted vegetation or to the seeds of the unwanted vegetation or to the area in which the unwanted vegetation grows, said formulation comprising said one or more compounds of formula (I) or salts thereof and at least one additional substance.

18. The method of claim 17, wherein said at least one additional substance comprises a solid or liquid carrier.

19. The method of claim 17, wherein said at least one additional substance comprises an agrochemically active substance that is different from the one or more compounds of formula (I) or salts thereof.

20. The method of claim 1, wherein the one or more compounds of formula (I) or salts thereof are applied to the unwanted vegetation or to the seeds of the unwanted vegetation or to the area in which the unwanted vegetation grows by spraying or by incorporation into soil that is in contact with the seeds or in which the unwanted vegetation is growing.

* * * * *